United States Patent [19]

Selwitz et al.

[11] 4,236,030

[45] Nov. 25, 1980

[54] PROCESS FOR RECOVERING PHENOLS FROM A HYDROCARBON MIXTURE CONTAINING THE SAME

[75] Inventors: Charles M. Selwitz, Monroeville; John G. McNulty, Glenshaw, both of Pa.

[73] Assignee: Gulf Research & Development Company, Pittsburgh, Pa.

[21] Appl. No.: 140

[22] Filed: Jan. 2, 1979

[51] Int. Cl.$^3$ ............................................. C07C 37/70
[52] U.S. Cl. .................................... 568/756; 568/750
[58] Field of Search ............... 568/751, 753, 750, 749, 568/756

[56] References Cited

U.S. PATENT DOCUMENTS

| | | | |
|---|---|---|---|
| 1,214,414 | 1/1917 | Berend | 568/749 |
| 2,433,143 | 12/1947 | Mohrman | 568/750 |
| 2,618,664 | 11/1952 | Hess et al. | 568/752 |
| 2,618,666 | 11/1952 | Hess et al. | 568/752 |
| 2,796,445 | 6/1957 | Sullivan | 568/727 |
| 2,917,487 | 12/1959 | Jones et al. | 568/750 |
| 4,081,485 | 3/1978 | Eguchi | 568/753 |

*Primary Examiner*—Werren B. Lone

[57] ABSTRACT

A process for recovering phenols from a hydrocarbon mixture containing the same which comprises extracting such mixture with an aqueous formaldehyde solution.

11 Claims, No Drawings

PROCESS FOR RECOVERING PHENOLS FROM A HYDROCARBON MIXTURE CONTAINING THE SAME

BACKGROUND OF THE INVENTION

1. Field of the Invention

The present invention is directed to a process for recovering phenols from a hydrocarbon mixture containing the same which comprises extracting said mixture with an aqueous formaldehyde solution.

2. Description of the Prior Art

The removal of phenols from a hydrocarbon mixture containing the same is appreciated in the art. Thus, Hess et al in U.S. Pat. No. 2,618,666, is interested in a process for isolating phenolic compounds from mixtures containing the same. An aromatic mixture, such as coal tar, is contacted with a water-soluble aliphatic polyamino compound, for example, alkylene diamines, polyalkylene diamines and mixtures thereof. The polyamino compounds complex with the phenolic compounds, forming a liquid complex phase which separates from the mixture in the presence of an anti-solvent selected from paraffinic and naphthenic hydrocarbons and mixtures thereof. This step is followed by contact of the liquid complex phase with a solvent, for example, an aliphatic ether, to decompose the liquid complex phase and separate the phenolic compounds from the polyamino compounds.

Another process is set forth in U.S. Pat. No. 2,618,664, also to Hess et al, which teaches the isolation of phenolic compounds, such as phenols, cresols, ethylphenols and xylenols, from aromatic mixtures, for example, coal tar. The process involves contacting the coal tar mixture, including tar acid, with aqueous hexamethylene tetramine in the presence of an anti-solvent, for example, paraffinic and naphthenic hydrocarbons, wherein said hexamethylene tetramine complexed with said phenolic compounds. Thereafter, the phenolic compounds are extracted from the complex mixture with a solvent, for example, ether.

SUMMARY OF THE INVENTION

We have found that phenols can be removed effectively and easily from a hydrocarbon mixture containing the same by extracting said mixture with an aqueous formaldehyde solution. By "phenols" we mean to include not only phenol itself but also those compounds containing a hydroxyl group attached to a single aromatic nucleus, as well as homologs of these compounds with one or more alkyl radicals directly attached to the aromatic nucleus, such as, for example, phenol, ortho-, meta- and para-cresols, ortho-, meta- and para-ethylphenols, 2,3-, 2,4-, 2,5-, 3,4-, and 3,5-xylenols, etc. The hydrocarbon mixtures containing phenols treated herein can be obtained from any suitable or conventional source, as, for example, from petroleum distillates boiling between about 150° to about 250° C. at ambient pressure, from tars produced from by-product coke ovens, from shale oils, from coal liquids resulting from the hydrogenation of coal, etc. In general the hydrocarbon mixture treated herein will have a boiling point range at ambient pressure of about 150° to about 250° C., preferably about 170° to about 220° C., and will contain from about five to about 80 weight percent, preferably from about 35 to about 80 weight percent, of the defined phenols.

In extracting the phenols from the hydrocarbon mixture, it is necessary only to contact such mixture with an aqueous formaldehyde solution, preferably in the presence of a paraffin hydrocarbon or mixtures of paraffin hydrocarbons, straight, branched or cyclic, having from four to eight, preferably from five to six carbon atoms. The weight ratio of aqueous formaldehyde solution to hydrocarbon mixture can vary over a wide range, for example, from about 10:1 to about 1:10, preferably from about 4:1 to about 1:2. The weight percent formaldehyde in the aqueous formaldehyde solution can be in the range of about 10 to about 70 percent, preferably about 20 to about 50 percent, most preferably about 35 to about 40 percent. Examples of paraffin hydrocarbons that can be used, if desired include butane, pentane, hexane, methyl pentanes, methyl cyclopentane, cyclohexane, isooctane, straight run naphtha, petroleum ether, etc. When these hydrocarbons are used, it is for the purpose of increasing selectivity of separation and to minimize the amount of non-phenolic compounds present in the recovered phenol phase. The hydrocarbons can be used in amounts such as to constitute up to about 60 weight percent of the final solution being treated, preferably about 15 to about 35 weight percent. The temperature of treatment can be in the range of about 0° to about 100° C., preferably about 15° to about 30° C., and the pressure about 0.1 to about 10 atmospheres (about 9.646 to about 964.6 kPa), or even higher, but preferably atmospheric pressure (ambient pressure), for a time in the range of about 0.1 to about 20 hours, preferably about 0.2 to about 2.0 hours. Any procedure that assures contact among the components in the final composition can be used. Particularly effective procedures involve conventional mixing or stirring using conventional stirring or mixing apparatus.

At the end of the extraction procedure defined above, the mixture will settle, for example, over a period of about 0.1 to about 20 hours, preferably a period of about 0.5 to about 2.0 hours, depending upon the amount of components therein, into two or three phases. In each case the top phase will contain the non-phenolic components of the hydrocarbon mixture, very small amounts of phenols and, when used, the paraffin hydrocarbon. When two layers are formed the lower layer will contain the desired phenols, formaldehyde and water. When three layers are formed, the desired phenols, along with small amounts of the non-phenolic components of the hydrocarbon mixture, formaldehyde, water and paraffin hydrocarbon, when used, will be in the middle layer. The top layer will be of the same composition as the top layer when two layers are formed and the bottom layer will contain small amounts of phenols, formaldehyde and most of the water. Separation of the layers so formed from each other can be effected in any convenient manner, for example, by decantation. Separation of the individual components from each other in the extract phase can also be effected in any convenient manner, for example, by distillation, at ambient pressure, in a temperature range of about 20° to about 250° C. If desired, however, this extract layer, containing substantially all of the formaldehyde and phenols, can be heated, for example, in the presence of a suitable catalyst, such as sulfuric acid, at a temperature of about 0° to about 100° C. and a pressure of about 0.1 to about 10 atmospheres (about 9.646 to about 964.6 kPa) for about 0.1 to about 10 hours, to obtain a phenol-formaldehyde resin.

DESCRIPTION OF PREFERRED EMBODIMENTS

The process defined and claimed herein can be further illustrated by the following wherein a coal liquid obtained by the hydrogenation of coal was subjected to extraction with an aqueous formaldehyde solution. The coal liquid was obtained as follows. A slurry containing crushed, dried coal and hydrocarbon process solvent was maintained at a temperature of about 390° to about 425° C. and a hydrogen pressure of about 2000 pounds per square inch gauge (13,785 kPa) for one hour. The reaction product was passed to a phase separator to remove vapors therefrom. The liquid was sent to a fractionation column wherein a naphtha fraction having a boiling range of about 71° to about 177° C. was removed overhead. The bottoms from this fractionator was sent to a centrifuge wherein solids, constituting mainly unreacted coal and ash, were removed therefrom. The liquids from the centrifuge were then sent to a vacuum distillation tower wherein an overhead cut boiling up to a temperature of about 260° C. was recovered. A portion of this latter cut was used as the slurring medium for the hydrogenation described above. Another portion of the overhead cut defined above was distilled at atmospheric pressure to obtain a cut boiling from 186° to 208° C. and is the hydrocarbon mixture subjected to extraction in the following runs. The hydrocarbon mixture was found to have the following analysis:

TABLE I

| Component | Weight Percent |
| --- | --- |
| Neutrals* | 53.9 |
| 2,6-xylenol | 0.2 |
| Nitrogen-containing compounds | 0.4 |
| Ortho-cresol | 6.1 |
| Phenol + ortho-cresol + ethyl phenol | 6.7 |
| 2,5-xylenol + para-cresol | 12.0 |
| Meta-cresol | 20.1 |
| Heavy components | 0.6 |

*Neutrals are hydrocarbons, predominantly aromatic, such as alkyl benzenes, indenes, naphthalenes, etc.

Three runs were carried out wherein the above hydrocarbon mixture, heptane and 37 percent formalin, was placed in a closed container, shaken vigorously for ten minutes at ambient conditions of temperature and pressure and allowed to stand for ten minutes. At the end of this time two layers separated in the first run and three in the remaining two runs. The layers were separated by drawing them off individually and analyzed by gas liquid chromatography. The results obtained are summarized below in Table II.

TABLE II

| Run No. | 1 | 2 | 3 |
| --- | --- | --- | --- |
| Charge, Gms | | | |
| Phenols | 0.75 | 3.25 | 5.00 |
| Neutrals | 0.60 | 2.60 | 4.00 |
| Heptane | 1.20 | 5.20 | 8.00 |
| Water | 3.50 | 3.50 | 3.50 |
| Formaldehyde | 2.00 | 2.00 | 2.00 |
| Weight Ratio of Aqueous Formaldehyde to Charge | 1:4 | 1:1 | 2:1 |
| Product | | | |
| Top Layer | | | |
| Heptane | 1.2 | 5.0 | 7.5 |
| Neutrals | 0.6 | 2.6 | 3.8 |
| Phenols | 0.1 | 0.1 | 1.7 |
| Formaldehyde | — | — | — |
| Water | — | — | — |
| Middle Layer | | | |
| Heptane | | 0.2 | 0.5 |
| Neutrals | | 0.1 | 0.2 |
| Phenols | None | 2.0 | 3.2 |
| Formaldehyde | | 0.8 | 1.4 |
| Water | | 0.8 | 0.6 |
| Lower Layer | | | |
| Heptane | — | — | — |
| Neutrals | — | — | — |
| Phenols | 0.65 | 1.0 | 0.1 |
| Formaldehyde | 2.0 | 1.2 | 0.6 |
| Water | 3.5 | 0.8 | 2.4 |
| Percent Phenols Separated From Neutrals | 87 | 97 | 66 |

The effectiveness of the process defined and claimed herein is apparent from the data in Table II. It will be seen that by selectively using an aqueous formaldehyde solution up to 97 percent of the phenols can be recovered from a hydrocarbon mixture containing the same. Since the layer containing the phenols also contains a substantial amount of the formaldehyde, it is apparent that the two need not be separated from each other if a resin composed of the two is desired. Thus, two milliliters of the middle layer from Run No. 2 was mixed with three drops of 98 percent aqueous sulfuric acid and heated for about three minutes at around 100° C. to produce a solid phenol formaldehyde resin.

Obviously, many modifications and variations of the invention, as hereinabove set forth, can be made without departing from the spirit and scope thereof, and, therefore, only such limitations should be imposed as are indicated in the appended claims.

We claim:

1. A process for recovering phenols selected from the group consisting of phenol and compounds containing a hydroxyl group and at least one alkyl radical attached to a single aromatic nucleus from a hydrocarbon mixture containing the same having a boiling point range of about 150° to about 250° C. and containing from about five to about 80 weight percent of said phenols which comprises extracting said mixture with an aqueous formaldehyde solution, wherein the weight ratio of aqueous formaldehyde solution to said hydrocarbon charge is in the range of about 10:1 to about 1:10, the weight percent formaldehyde in said aqueous formaldehyde solution is in the range of about 10 to about 70 percent, and said extraction is carried out at a temperature of about 0° to about 100° C. and a pressure of about 0.1 to about 10 atmospheres for about 0.1 to about 20 hours.

2. The process of claim 1 wherein the weight ratio of aqueous formaldehyde solution to said hydrocarbon charge is in the range of about 4:1 to about 1:2.

3. The process of claim 1 wherein the weight percent formaldehyde in said aqueous formaldehyde solution is in the range of about 20 to about 50 percent.

4. The process of claim 1 wherein the weight percent formaldehyde in said aqueous formaldehyde solution is in the range of about 35 to about 40 percent.

5. The process of claim 1 wherein said extraction is carried out at a temperature of about 15° to about 30° C. and a pressure of about one atmosphere for about 0.2 to about 2.0 hours.

6. The process of claim 1 wherein the mixture during said extraction also contains up to about 60 weight percent of a paraffin hydrocarbon having from four to eight carbon atoms.

7. The process of claim 1 wherein the mixture during said extraction also contains from about 15 to about 35 weight percent of a paraffin hydrocarbon having from five to six carbon atoms.

8. The process of claim 1 wherein the mixture during the extraction also contains heptane.

9. The process of claim 1 wherein the weight ratio of aqueous formaldehyde solution to said hydrocarbon charge is in the range of about 4:1 to about 1:2, the weight percent formaldehyde in said aqueous formaldehyde solution is in the range of about 20 to about 50 percent, the temperature is in the range of about 15° to about 30° C., the pressure is about one atmosphere, the contact time is about 0.2 to about 2.0 hours and the mixture during the extraction contains from about 15 to about 35 weight percent of a paraffin hydrocarbon having from five to six carbon atoms.

10. The process of claim 1 wherein said hydrocarbon mixture has a boiling point range of about 170° to about 220° C. and contains from about 35 to about 80 weight percent phenols.

11. The process of claim 1 wherein said hydrocarbon mixture is obtained from coal liquids resulting from the hydrogenation of coal.

* * * * *